(12) United States Patent
Eisenbraun

(10) Patent No.: US 6,416,043 B1
(45) Date of Patent: Jul. 9, 2002

(54) LOUVER AIR FRESHENER

(76) Inventor: Kenneth D. Eisenbraun, 485 N. Cranbrook Rd., Bloomfield Village, MI (US) 48301

( * ) Notice: Subject to any disclaimer, the term of this patent is extended or adjusted under 35 U.S.C. 154(b) by 14 days.

(21) Appl. No.: 09/664,675

(22) Filed: Sep. 19, 2000

Related U.S. Application Data

(63) Continuation-in-part of application No. 29/122,642, filed on May 2, 2000, now Pat. No. Des. 437,041.

(51) Int. Cl.[7] .................................................. B01F 3/04
(52) U.S. Cl. ............................. 261/104; 261/DIG. 88; 422/123
(58) Field of Search ...................... 261/104, DIG. 88; 422/123, 124; 239/53, 54, 55, 56, 57, 58, 59, 60; D23/366

(56) References Cited

U.S. PATENT DOCUMENTS

| | | | |
|---|---|---|---|
| 4,647,433 A | 3/1987 | Spector | 422/125 |
| 5,269,723 A | 12/1993 | Bender | 454/157 |
| 5,368,822 A | 11/1994 | McNeil | 422/124 |
| 5,465,521 A | 11/1995 | Baker et al. | 43/1 |
| 5,704,832 A | 1/1998 | Borrell | 454/157 |
| 5,865,372 A | 2/1999 | Ceresko | 239/60 |
| 6,102,660 A | * 8/2000 | Lee | 416/146 R |
| 6,103,201 A | * 8/2000 | Green | 422/124 |

* cited by examiner

*Primary Examiner*—Robert A. Hopkins
(74) *Attorney, Agent, or Firm*—Gifford, Krass, Groh, Sprinkle, Anderson & Citkowski, P.C.

(57) ABSTRACT

An air freshener includes a frame having a clip, the clip for attachment to a vehicle air duct louver and a deflector extending external to the louver into the passenger compartment. The deflector fluttering under operation of a vehicle climate control system to further promote aroma dispersion. The deflector being swivel mounted to the clip.

11 Claims, 2 Drawing Sheets

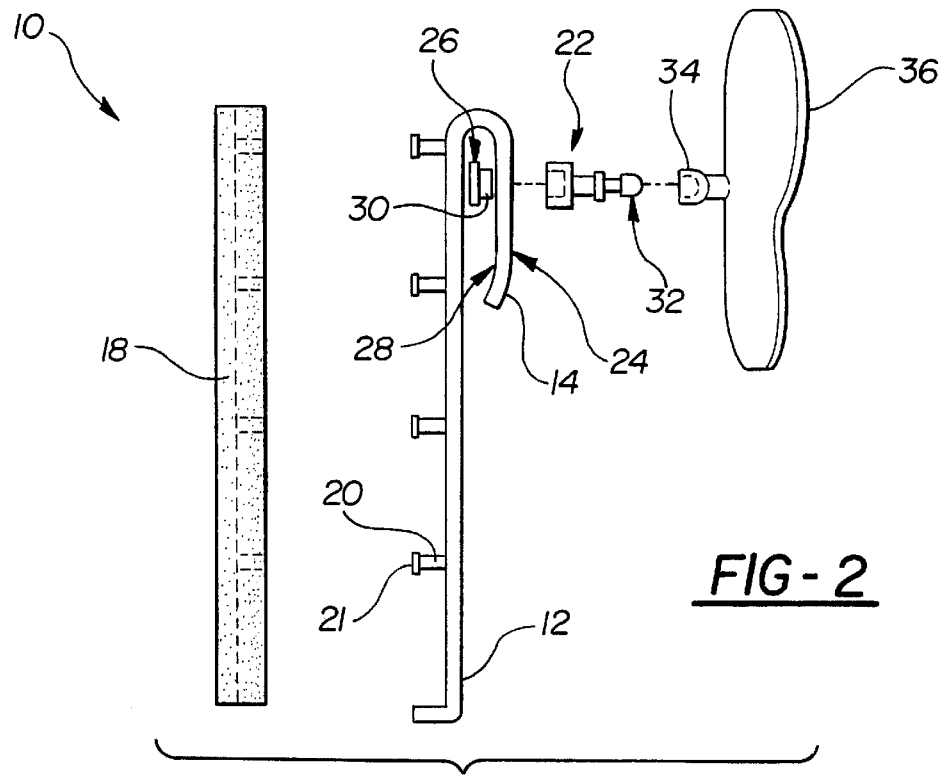
FIG-2
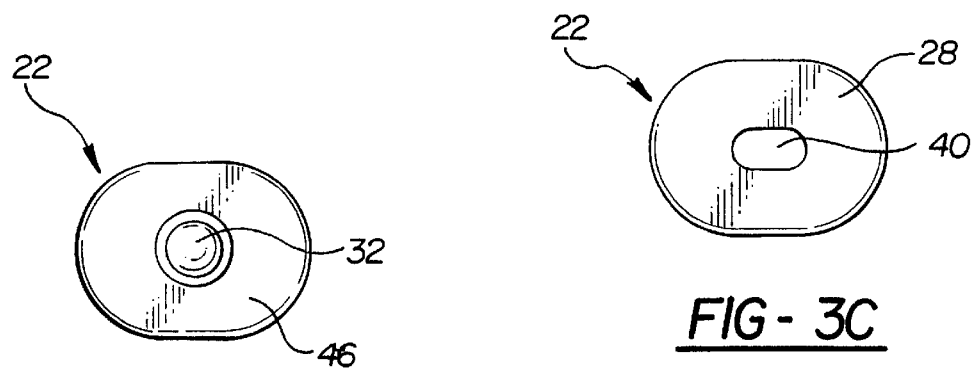
FIG-3A
FIG-3C
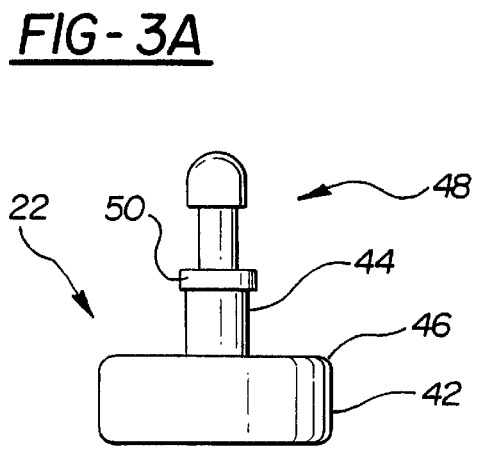
FIG-3B
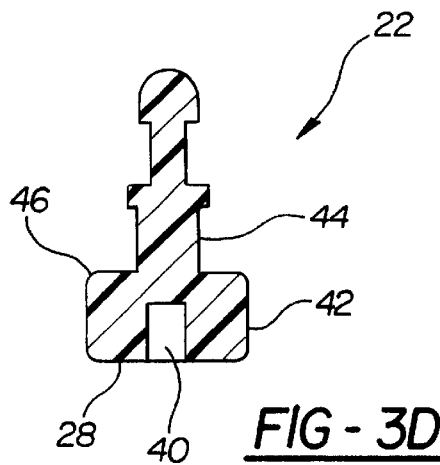
FIG-3D

LOUVER AIR FRESHENER

RELATED APPLICATION

This application is a continuation-in-part of U.S. Design patent application Ser. No. 29/122,642 filed May 2, 2000, now U.S. Pat. Design No. 437,041.

FIELD OF THE INVENTION

The present invention relates to air fresheners and, more particularly, to an air freshener adapted to engage a vehicle air duct louver.

BACKGROUND OF THE INVENTION

Owing to traffic congestion and urban sprawl, commuters are spending ever-increasing amounts of time in vehicles. As a result of increased residence time in vehicles, commuters often consume food and drink in vehicles. The spillage of consumables has made an air freshener a common accessory in the passenger compartment of a vehicle. Vehicle air fresheners are commonly affixed to a vehicle console proximal to an air duct such that the vehicle climate control system conveys a masking aroma throughout the passenger compartment. The aroma being impregnated within the air freshener. Examples of conventional air fresheners are disclosed in U.S. Pat. Nos. 5,269,723; 5,368,822; 5,465,521; 5,704,832 and 5,865,372.

Conventional air fresheners that engage a vehicle air duct louver are advantageous in being readily affixed to the air duct, as well as having good laminar flow of air across the aroma releasing surface of the air freshener. However, a louver attached air freshener is limited in its utility owing to the directionality of air exiting a vehicle air duct. As a result, to fully aromatize the passenger compartment of a vehicle, several air fresheners are often dispersed among the climate control ducts of a vehicle. Thus, there exists a need for a louver mountable air freshener capable of dispersing an aroma over a substantial vehicle passenger compartment volume.

SUMMARY OF THE INVENTION

An air freshener for mounting on a vehicle climate control louver includes a frame terminating in a clip adapted to engage the louver. An airflow deflector swivelably extends from an elongated aperture in the clip. An aroma emanates from the inventive air freshener and is dispersed by the deflector.

BRIEF DESCRIPTION OF THE DRAWINGS

FIG. 2 is an exploded side view of the air freshener according to the present invention; and FIGS. 3A–D are top, side, bottom, and cutaway views, respectively, of a swivel tab according to FIG. 1.

DETAILED DESCRIPTION OF THE PREFERRED EMBODIMENTS

Figure 1:
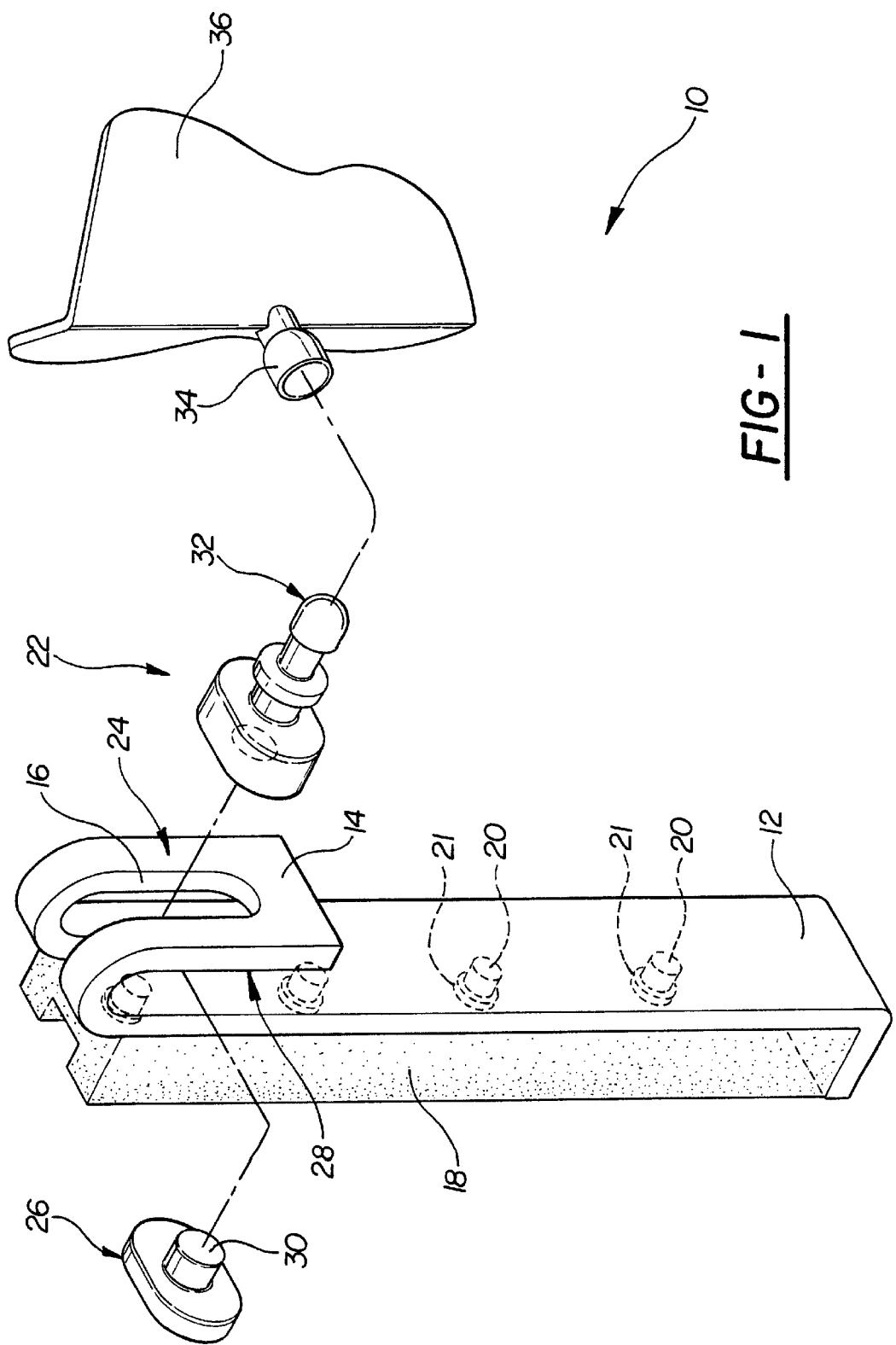
FIG. 1 is an exploded perspective view of an air freshener according to the present invention.

The present invention has utility as a vehicle louver attachable air freshener having a deflector extending from the louver in order to disperse aromatized air within a vehicle passenger compartment. A deflector is mounted to an air freshener according to the present invention using a swivel to provide compact storage and deflection control of aromatized airflow.

Referring now to FIGS. 1 and 2, an air freshener 10 according to the present invention includes a rigid polymeric frame 12. As used herein, "rigid" is defined as a modulus of rigidity at least greater than 20% of the modulus for atactic polyethylene. The frame 12 terminates in a clip 14 having a sufficient length to engage a vehicle louver slat. The clip portion 14 has an elongated aperture 16 therein. A frame according to the present invention is preferably injected molded of a thermoplastic illustratively including polyalkenes, polycarbonate and polystyrene. Attached to the frame 12 is an aroma impregnated strip 18. The aroma impregnated strip 18 is adhered to the frame 12 by a series of posts 20 of the frame 12 extending through apertures 21 in the strip 18. It is appreciated that an aroma impregnated strip is readily adhered to a frame by other conventional techniques illustratively including adhesives, thermal fusion, solvent welding and the like. An aroma impregnated strip preferably is constructed of an open cell polymeric matrix incorporating solvated globules of the aroma. Strip matrix materials illustratively include polyvinyl chloride, EVA, K-resins and polyalkenes. Any desired aroma may be impregnated within a strip either in pure form or solvated by solvents illustratively including water, alcohol, esters, ketones, and other organic solvents. Aromas illustratively include vanilla, pine oil, and citrus. A swivel 22 contacts the outer surface 24 of the clip 14. The swivel 22 is held in contact with the elongated aperture 16 of the clip 14 by way of a snap button 26 press fit into the rearward surface 28 of the swivel 22. Thus, the snap button 26 engages the elongated aperture 16 and the swivel 22. The snap button 26 has a head 30 having dimensions sufficiently large to prevent the head 30 from passing through the elongated aperture 16 and a shaft 31 adapted to engage the rearward surface 28 of the swivel 22. The outward surface 32 of the swivel 22 is adapted to engage a complementary fitting 34 of a flattened deflector 36. Preferably, the swivel 22 and the snap button 26 are formed from one of the same materials from which the frame 12 is formed. More preferably, the swivel 22 and snap button 26 are formed of the same material as the frame 12. While the swivel 22 and snap button 26 are elliptical in cross section, it is appreciated that other complementary shapes are operative herein to form a deflector swivel mount.

A deflector according to the present invention is formed to any shape capable of redirecting airflow from a vehicle air duct. Illustrative deflector configurations include a flattened disc, a rotatable propeller shape, and irregularly shaped sheets. Additionally, a deflector readily assumes ornamental deflector shapes illustratively including a butterfly, a hat, a figure silhouette, figure silhouettes and the like. Optionally, a deflector according to the present invention has an additional joint (not shown) intermediate between the deflector and the swivel engaging fitting. An additional joint affords greater adjustment control over airflow direction exiting a vehicle air duct equipped with an air freshener according to the present invention. A deflector according to the present invention is formed from a variety of materials illustratively including metal, plastic, wood and laminates thereof. Preferred plastics or the formation of a deflector are polyacetate and polyalkenes. In a preferred embodiment, the deflector has a thickness from about 0.3 to 5 millimeters and sufficient flexibility to flutter under the force of air duct flow. In a further preferred embodiment the deflector is a sheet material having an edge. Flutter of a deflector according to the present invention serves to further promote dispersion of aromatized air within the vehicle passenger compartment. Preferably, the deflector edge flutters more than 0.5% of the deflector edge thickness under the force of vehicle climate control airflow at the lowest operative climate control fan speed.

FIGS. 3A–D depict various views of the air freshener swivel according to the present invention. The swivel 22 has a bore hole 40 in the rearward surface 28. The bore hole 40 is adapted to frictionally seat the shaft 31 of snap button 26. Preferably, the bore hole 40 is oval in cross section to facilitate frictional interaction with the shaft 31 Optionally, bore hole 40 is decorated along the walls thereof with friction increasing structures illustratively including ridges, threads, and dimples. The bore hole 40 extends into the base portion 42 of the swivel 22. A columnar portion 44 extends from the base 42 thereby defining a shoulder 46. A male fitting 48 extends from the columnar portion 44 thereby forming a second shoulder 50. The male fitting 48 is adapted to frictionally engage a fitting 34 of deflector. 36 as shown in FIG. 1.

Patents and publications mentioned in the specification are indicative of the levels of those skilled in the art to which the invention pertains. These patents and publications are incorporated herein by reference to the same extent as if each individual patent or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

What is claimed is:

1. An air freshener for mounting on a vehicle climate control louver comprising:

a frame terminating in a clip, the clip adapted to engage the louver and having an elongated aperture therein;

an aroma impregnated portion adhered to the frame; and an airflow deflector slidably extending from the elongated aperture.

2. The air freshener of claim 1 wherein said deflector is attached to a swivel having a rearward surface, the rearward surface having a bore hole therein, said swivel held in slideable engagement with the elongated aperture by a snap button having a shaft complementary to the bore hole.

3. The air freshener of claim 2 wherein the bore hole and the shaft have noncircular cross sections.

4. The air freshener of claim 1 wherein the aroma impregnated portion is a strip.

5. The air freshener of claim 4 wherein said aroma impregnated strip is attached to said frame by a plurality of posts extending from said frame and through complementary apertures in said strip.

6. The air freshener of claim 1 wherein said deflector is a sheet material having an edge.

7. The air freshener of claim 6 wherein said sheet material has a thickness between 0.3 and 5 millimeters.

8. The air freshener of claim 6 wherein the deflector sheet material is flexible such that the edge flutters more than 0.5% of the deflector edge thickness under the force of vehicle climate control airflow at the lowest operative climate control fan speed.

9. An improved air freshener for mounting on a vehicle climate control louver having a frame portion that engages the louver, and an aroma emitting portion adhered to the frame wherein the improvement lies in an airflow deflector swivellably attached to said frame.

10. The improved air freshener of claim 9 wherein the further improvement lies in said deflector being composed of a sheet material that flutters in response to the force of airflow from the vehicle climate control under the lowest operable fan speed.

11. The improved air freshener of claim 9 wherein the deflector has a thickness is between 0.3 and 5 millimeters.

\* \* \* \* \*